(12) United States Patent
Chen et al.

(10) Patent No.: US 11,371,962 B1
(45) Date of Patent: Jun. 28, 2022

(54) MULTI-FREQUENCY ACOUSTIC VELOCITY MEASUREMENT DEVICE FOR CORE

(71) Applicants: Southwest Petroleum University, Chengdu (CN); Haohan Well Completion & Logging Science and Techonlogy Limited Company, Chengdu (CN)

(72) Inventors: Yijian Chen, Chengdu (CN); Xingyu Chen, Chengdu (CN); Gao Li, Chengdu (CN); Lunping Zhang, Chengdu (CN); Chaofan Tu, Chengdu (CN); Yunsheng Chen, Chengdu (CN); Kejing Wang, Chengdu (CN)

(73) Assignees: SOUTHWEST PETROLEUM UNIVERSITY, Chengdu (CN); HAOHAN WELL COMPLETIONGLOGGING SCIENCE AND TECHNOLOGY LIMITED COMPANY, Chengdu (CN)

( * ) Notice: Subject to any disclaimer, the term of this patent is extended or adjusted under 35 U.S.C. 154(b) by 0 days.

(21) Appl. No.: 17/646,151

(22) Filed: Dec. 28, 2021

(30) Foreign Application Priority Data

Sep. 10, 2021 (CN) .......................... 202111065511.8

(51) Int. Cl.
*G01N 29/07* (2006.01)
*G01N 33/24* (2006.01)
*G01N 29/34* (2006.01)

(52) U.S. Cl.
CPC ........... *G01N 29/07* (2013.01); *G01N 29/345* (2013.01); *G01N 33/241* (2013.01); *G01N 2291/011* (2013.01)

(58) Field of Classification Search
CPC ...... G01N 29/07; G01N 29/345; G01N 29/04; G01N 33/241; G01N 33/388; G01N 2291/011
See application file for complete search history.

(56) References Cited

U.S. PATENT DOCUMENTS

| 6,112,599 A | * | 9/2000 | Maki, Jr. | ................ G01N 29/30 73/587 |
| 2009/0166033 A1 | * | 7/2009 | Brouwer | ................ E21B 47/00 703/2 |

(Continued)

FOREIGN PATENT DOCUMENTS

CN 204461598 U 7/2015

OTHER PUBLICATIONS

Liu Zhu-Ping, et al., Laboratory Study of Acoustic Parameters of Rock, Acta Geophysica Sinica, 1994, pp. 659-666, vol. 37, No. 5.

(Continued)

*Primary Examiner* — Suman K Nath
(74) *Attorney, Agent, or Firm* — Bayramoglu Law Offices LLC

(57) ABSTRACT

A multi-frequency acoustic velocity measurement device for a core includes: a fixing device, for fixing a core and heating and pressurizing the core according to a preset condition; a transmitting end acoustic wave probe, connected to a first end of a control unit and one end of the fixing device, and configured to transmit an acoustic wave signal to the core; a receiving end acoustic wave probe, connected to a second end of the control unit and the other end of the fixing device, and configured to receive the acoustic wave signal transmitted by the transmitting end acoustic wave probe; and the control unit, for controlling the transmitting end acoustic wave probe to transmit acoustic wave signals of different frequencies, receiving the acoustic wave signal received by (Continued)

the receiving end acoustic wave probe, and determining an acoustic velocity of the core according to the acoustic wave signal.

3 Claims, 1 Drawing Sheet

(56) References Cited

U.S. PATENT DOCUMENTS

2016/0109603 A1* 4/2016 Jin .......................... E21B 49/06
 73/152.58
2017/0342827 A1* 11/2017 Al-Qahtani ........... E21B 49/088

OTHER PUBLICATIONS

University Physics Experiment, 2008, pp. 142.
Clinical Ultrasound Imaging Diagnostics, 2018, pp. 35.
Zongwen Duan, Clinical Ultrasound Medicine, 2017, pp. 55.

* cited by examiner

MULTI-FREQUENCY ACOUSTIC VELOCITY MEASUREMENT DEVICE FOR CORE

CROSS REFERENCE TO THE RELATED APPLICATIONS

This application is based upon and claims priority to Chinese Patent Application No. 202111065511.8, filed on Sep. 10, 2021, the entire contents of which are incorporated herein by reference.

TECHNICAL FIELD

The present disclosure belongs to the technical field of acoustic velocity measurement of cores, and in particular relates to a multi-frequency acoustic velocity measurement device for a core.

BACKGROUND

The fluid in rock pores will cause acoustic dispersion, and the phenomenon of acoustic dispersion varies with different fluid content in the pores. For example, the acoustic velocity of a high-porosity, high-permeability sandstone core with a porosity of 35% and a permeability of $8.7 \times 10^{-12}$ m$^2$ was measured by using a stress-strain method and an ultrasonic measurement technology under different saturations. The measurement results show that when the saturation reached 90%, the difference between the velocities obtained by the ultrasonic measurement technology and the low-frequency measurement technology was up to 32%. In order to study the effect of pore fluid on the acoustic velocity of cores with different permeability, the stress-strain method is typically used to measure the acoustic velocity in the 2-2,000 Hz frequency band, and the ultrasonic pulse penetration method is used to measure the acoustic velocity at high frequencies.

One of the most important geophysical tasks in oil and gas exploration is reservoir prediction and hydrocarbon detection by utilizing seismic data. The selection of sensitive seismic attributes relies on solid and reliable petrophysical research work in the study area, and the acoustic velocity measurement of the core is one of the most important petrophysical work. The multi-frequency measurement method in the present disclosure is intended to measure and analyze the acoustic dispersion of the core, which overcomes the problem of frequently replacing acoustic wave probes of different frequencies during measurement, and reduces the cost of experimental measurement and the difficulty of operation.

The acoustic velocity measurement method of the core in the prior art can only measure the acoustic velocity at a single frequency, and thus it is necessary to replace the acoustic wave probes with different center frequencies so as to measure the acoustic velocity of the core at multiple frequencies, which is time-consuming. In addition, the center frequency intervals of the probes are large, and the acoustic wave probe cannot be replaced under high-temperature and high-pressure conditions.

Therefore, the rapid acoustic velocity measurement of the core under the conditions of high temperature, high pressure and multiple frequencies is a technical problem to be solved by those skilled in the art.

SUMMARY

In order to solve the technical problem that the prior art cannot rapidly measure the acoustic velocity of a core under high temperature, high pressure and multi-frequency conditions, an objective of the present disclosure is to provide a multi-frequency acoustic velocity measurement device for a core.

The present disclosure adopts the following technical solution: a multi-frequency acoustic velocity measurement device for a core, including:

a fixing device, for fixing a core and heating and pressurizing the core according to a preset condition;

a transmitting end acoustic wave probe, where the transmitting end acoustic wave probe is connected to a first end of a control unit and one end of the fixing device; the transmitting end acoustic wave probe is further connected to a receiving end acoustic wave probe; and the transmitting end acoustic wave probe is configured to transmit a first acoustic wave signal to the core and a second acoustic wave signal to the receiving end acoustic wave probe;

the receiving end acoustic wave probe, where the receiving end acoustic wave probe is connected to a second end of the control unit and the other end of the fixing device; and the receiving end acoustic wave probe is configured to receive the second acoustic wave signal and the first acoustic wave signal passing through the core; and the control unit, for controlling the transmitting end acoustic wave probe to transmit acoustic wave signals of different frequencies, receiving the first acoustic wave signal and the second acoustic wave signal received by the receiving end acoustic wave probe, and determining an acoustic velocity of the core according to the acoustic wave signals received by the receiving end acoustic wave probe.

Further, the first end of the control unit may be a transmitted signal amplifying circuit, and the second end of the control unit may be a received signal amplifying circuit.

Further, the control unit may include a controller and a transmission control area; the transmission control area may include a single-chip microcomputer (SCM), a signal generator and the transmitted signal amplifying circuit connected in sequence; and the controller may be connected to the SCM, where:

the SCM may be configured to parse an instruction issued by the controller, and send the parsed instruction to the signal generator;

the signal generator may be configured to generate a corresponding sine wave signal according to the parsed instruction, and send the sine wave signal to the transmitted signal amplifying circuit; and the transmitted signal amplifying circuit may be configured to amplify the sine wave signal, and send the amplified sine wave signal to the transmitting end acoustic wave probe, such that the transmitting end acoustic wave probe transmits the sine wave signal as an acoustic wave signal to the core and the receiving end acoustic wave probe.

Further, the control unit further may include a receiving control area; the receiving control area may include the received signal amplifying circuit and a data acquisition circuit connected in sequence; and the data acquisition circuit may be further connected to the controller and the SCM, where:

the received signal amplifying circuit may be configured to amplify the first acoustic wave signal received by the receiving end acoustic wave probe, and send the amplified first acoustic wave signal to the data acquisition circuit; and the data acquisition circuit receives an adjustment instruction from the SCM, and may be configured to acquire the second acoustic wave signal and the amplified first acoustic wave signal of different frequencies received by the receiving end acoustic wave probe.

Further, the data acquisition circuit may be further configured to:

normalize the acquired first acoustic wave signal and second acoustic wave signal into a normalized signal;

filter an alternating current (AC) signal in the normalized signal through a filter in the data acquisition circuit to acquire a direct current (DC) signal; and send the DC signal to the controller.

Further, the control unit determines the acoustic velocity of the core according to the acoustic wave signals received by the receiving end acoustic wave probe by:

determining a time for the first acoustic wave signal to pass through the core; and determining the acoustic velocity based on the time and a length of the core.

Further, the time for the first acoustic wave signal to pass through the core may be determined by:

$$S=\sin(2\pi f(t+kT));$$

where, S is the DC signal; f is a frequency of the first acoustic wave signal; t is the time for the first acoustic wave signal to pass through the core; k is a number of cycles of the first acoustic wave signal; and T is a cycle at a corresponding frequency.

Compared with the prior art, the present disclosure has the following beneficial effects:

(1) The present disclosure provides a multi-frequency acoustic velocity measurement device for a core. The measurement device includes: a fixing device, for fixing a core and heating and pressurizing the core according to a preset condition; a transmitting end acoustic wave probe, connected to a first end of a control unit and one end of the fixing device, and configured to transmit an acoustic wave signal to the core; a receiving end acoustic wave probe, connected to a second end of the control unit and the other end of the fixing device, and configured to receive the acoustic wave signal transmitted by the transmitting end acoustic wave probe; and the control unit, for controlling the transmitting end acoustic wave probe to transmit acoustic wave signals of different frequencies, receiving the acoustic wave signal received by the receiving end acoustic wave probe, and determining an acoustic velocity of the core according to the acoustic wave signal received by the receiving end acoustic wave probe. The present disclosure achieves rapid measurement of the acoustic velocity of the core under high temperature, high pressure and multi-frequency conditions.

(2) In the multi-frequency acoustic velocity measurement device for a core, the transmission control area includes an SCM, a signal generator and a transmitted signal amplifying circuit connected in sequence. The controller is connected to the SCM, and the SCM parses an instruction issued by the controller, and sends the parsed instruction to the signal generator. The signal generator sends a corresponding sine wave signal according to the parsed instruction. The present disclosure can acquire acoustic wave signals of different frequencies and can achieve multi-frequency measurement of the acoustic velocity of a core without replacing the acoustic wave probe.

DETAILED DESCRIPTION OF THE EMBODIMENTS

The technical solutions in the embodiments of the present disclosure are clearly and completely described below with reference to the drawings in the embodiments of the present disclosure. The described embodiments are merely some rather than all of the embodiments of the present disclosure. All other embodiments obtained by those of ordinary skill in the art based on the embodiments of the present disclosure without creative efforts should fall within the protection scope of the present disclosure.

As mentioned in the background, the prior art cannot rapidly measure the acoustic velocity of a core under high temperature, high pressure and multi-frequency conditions.

Figure 1:
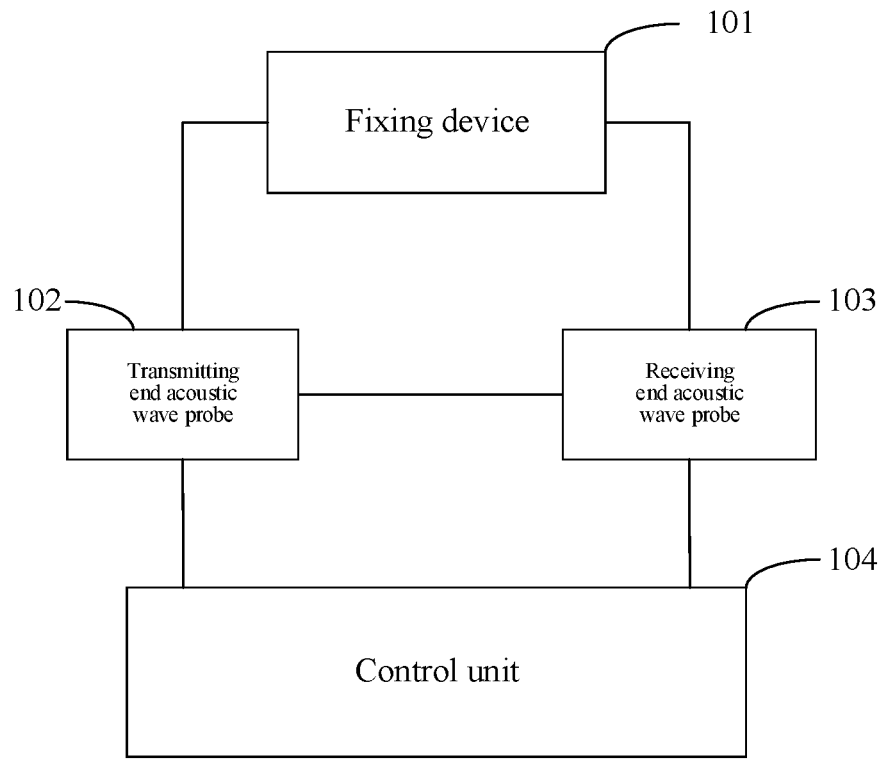
FIG. 1 is a structural view of a multi-frequency acoustic velocity measurement device for a core according to an embodiment of the present disclosure.

In view of this, the present disclosure provides a multi-frequency acoustic velocity measurement device for a core. FIG. 1 is a structural view of the multi-frequency acoustic velocity measurement device for a core according to an embodiment of the by the disclosure. The multi-frequency acoustic velocity measurement device includes:

a fixing device 101, for fixing a core and heating and pressurizing the core according to a preset condition;

a transmitting end acoustic wave probe 102, where the transmitting end acoustic wave probe 102 is connected to a first end of a control unit 104 and one end of the fixing device 101;

the transmitting end acoustic wave probe 102 is further connected to a receiving end acoustic wave probe 103; and the transmitting end acoustic wave probe 102 is configured to transmit a first acoustic wave signal to the core and a second acoustic wave signal to the receiving end acoustic wave probe 103;

the receiving end acoustic wave probe 103, where the receiving end acoustic wave probe 103 is connected to a second end of the control unit 104 and the other end of the fixing device 101; and the receiving end acoustic wave probe 103 is configured to receive the second acoustic wave signal and the first acoustic wave signal passing through the core; and the control unit 104, for controlling the transmitting end acoustic wave probe 102 to transmit acoustic wave signals of different frequencies, receiving the first acoustic wave signal and the second acoustic wave signal received by the receiving end acoustic wave probe 103, and determining an acoustic velocity of the core according to the acoustic wave signals received by the receiving end acoustic wave probe 103.

Specifically, the fixing device may be any type of fixing device in the art, for example, the device proposed by Chinese Patent Application CN200720081615.7. The preset condition may be a specified temperature and pressure. The present disclosure may be implemented under a high temperature and high pressure condition and a normal temperature and normal pressure condition.

In the embodiment of the present disclosure, the first end of the control unit 104 is specifically a transmitted signal amplifying circuit, and the second end of the control unit is specifically a received signal amplifying circuit.

Figure 2:
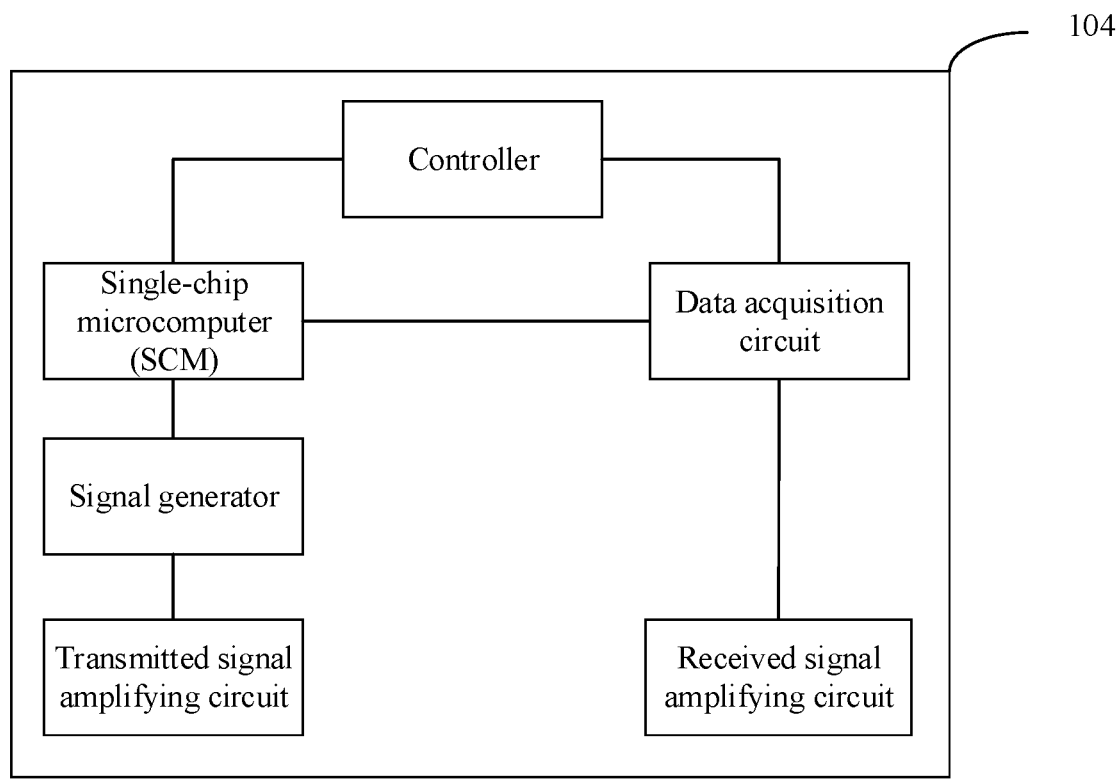
FIG. 2 is a structural view of a control unit according to an embodiment of the present disclosure.

In the embodiment of the present disclosure, the control unit 104 specifically includes a controller and a transmission control area. As shown in FIG. 2, a structural view of the control unit according to the embodiment of the present disclosure, the transmission control area specifically includes a single-chip microcomputer (SCM), a signal generator and the transmitted signal amplifying circuit connected in sequence; and the controller is connected to the SCM.

The SCM is configured to parse an instruction issued by the controller, and send the parsed instruction to the signal generator.

The signal generator is configured to generate a corresponding sine wave signal according to the parsed instruction, and send the sine wave signal to the transmitted circuit amplifying circuit.

The transmitted signal amplifying circuit is configured to amplify the sine wave signal, and send the amplified sine wave signal to the transmitting end acoustic wave probe 102, such that the transmitting end acoustic wave probe 102 transmits the sine wave signal as an acoustic wave signal to the core and the receiving end acoustic wave probe 103.

Specifically, in the present disclosure, the transmitted acoustic wave is acquired by a continuous sine-wave excited acoustic wave probe. The frequency of the transmitted acoustic wave is the same as the frequency of the sine wave that excites the acoustic wave probe (Note: If a pulse signal is used to excite the acoustic wave probe, the frequency of the transmitted acoustic wave is the same as the center frequency of the acoustic wave probe). Therefore, by changing the frequency of the exciting sine wave signal, acoustic waves of different frequencies can be acquired. Meanwhile, in order to ensure that the signal amplitude at a transmitting end remains basically unchanged with the change of frequency, the center frequency of the selected acoustic wave probe must be much greater than the frequency to be measured in the experiment. Therefore, a high-voltage signal is required to drive the acoustic wave probe. In this field, the signal generator and the transmitted signal amplifying circuit are usually combined together as a high-voltage signal generator, and the high-voltage signal generator generates a high-voltage signal above 50 V to drive the acoustic wave probe. The specific high-voltage signal may be flexibly set by those skilled in the art according to actual conditions to ensure the signal strength at the transmitting end, such that the receiving end acoustic wave probe 103 can receive an obvious signal.

In the embodiment of the present disclosure, the control unit 104 further includes a receiving control area. As shown in FIG. 2, a structural view of the control unit according to the embodiment of the present disclosure, the receiving control area includes the received signal amplifying circuit and a data acquisition circuit connected in sequence; and the data acquisition circuit is further connected to the controller and the SCM.

The received signal amplifying circuit is configured to amplify the first acoustic wave signal received by the receiving end acoustic wave probe 103, and send the amplified first acoustic wave signal to the data acquisition circuit.

The data acquisition circuit receives an adjustment instruction from the SCM, and is configured to acquire the second acoustic wave signal and the amplified first acoustic wave signal of different frequencies received by the receiving end acoustic wave probe 103.

In the embodiment of the present disclosure, the data acquisition circuit is further configured to:

normalize the acquired first acoustic wave signal and second acoustic wave signal into a normalized signal;

filter an alternating current (AC) signal in the normalized signal through a filter in the data acquisition circuit to acquire a direct current (DC) signal; and send the DC signal to the controller.

Specifically, the data acquisition circuit is an analog/digital (AD) acquisition circuit, which acquires two signals, namely a transmitting end signal, that is, the first acoustic wave signal, and a receiving end signal, that is, the second acoustic wave signal. The signal amplitude at the transmitting end will gradually increase as the frequency approaches the center frequency, and the attenuation of signals of different frequencies in the core is different. Therefore, it is necessary to normalize the data acquired by the two channels of the AD acquisition unit. In the present disclosure, the corresponding normalization coefficients at different frequencies are obtained by extracting the signal envelope, and the two normalized signals are multiplied to acquire a signal. An AC signal in the acquired signal is filtered through a filter to acquire a DC signal, which is related to the time for signals of different frequencies to pass through the core.

The control unit determines the acoustic velocity of the core according to the acoustic wave signals received by the receiving end acoustic wave probe by:

determining a time for the first acoustic wave signal to pass through the core; and determining the acoustic velocity based on the time and a length of the core.

This step is implemented by a controller in the control unit 104.

In the embodiment of the present disclosure, the time for the first acoustic wave signal to pass through the core is specifically determined by:

$$S=\sin(2\pi f(t+kT));$$

where, S is the DC signal; f is a frequency of the first acoustic wave signal; t is the time for the first acoustic wave signal to pass through the core; k is a number of cycles of the first acoustic wave signal; and T is a cycle at a corresponding frequency.

Specifically, in $S=\sin(2\pi f(t+kT))$, S is the DC signal; f is a frequency of the first acoustic wave signal; t is the time for the first acoustic wave signal to pass through the core; k is a number of cycles of the first acoustic wave signal; and T is a cycle at a corresponding frequency. Since the measurement starts from a low frequency and a frequency sweep method is adopted, the initial t will not exceed one cycle. That is, k is 0 at this low frequency, and the change of t is gradual. Based on the law of this gradual change, the value of k in the relationship between t and S after the frequency is increased can be determined.

The length of the core can be directly measured by using a tool, and then the acoustic velocity of the core can be calculated according to the following equation: distance (L)=velocity (v)*time (t).

Those of ordinary skill in the art will understand that the embodiments described herein are intended to help readers understand the principles of the present disclosure, and it should be understood that the protection scope of the present disclosure is not limited to such special statements and embodiments. Those of ordinary skill in the art may make other various specific modifications and combinations according to the technical teachings disclosed in the present disclosure without departing from the essence of the present disclosure, and such modifications and combinations still fall within the protection scope of the present disclosure.

What is claimed is:

1. A multi-frequency acoustic velocity measurement device for a core, comprising:

a fixing device, for fixing a core and for heating and pressurizing the core according to a preset condition;

a transmitting end acoustic wave probe, wherein the transmitting end acoustic wave probe is connected to a first end of a control unit and a first end of the fixing device; the transmitting end acoustic wave probe is further connected to a receiving end acoustic wave probe; and the transmitting end acoustic wave probe is configured to transmit a first acoustic wave signal to the core and transmit a second acoustic wave signal to the receiving end acoustic wave probe; the transmitting end acoustic wave probe is a continuous sine-wave excited acoustic wave probe;

the receiving end acoustic wave probe, wherein the receiving end acoustic wave probe is connected to a second end of the control unit and a second end of the fixing device; and the receiving end acoustic wave probe is configured to receive the second acoustic wave signal and the first acoustic wave signal passing through the core;

the control unit, for controlling the transmitting end acoustic wave probe to transmit acoustic wave signals of different frequencies, receiving the first acoustic wave signal and the second acoustic wave signal received by the receiving end acoustic wave probe, and determining an acoustic velocity of the core according to the acoustic wave signals received by the receiving end acoustic wave probe;

the first end of the control unit is a transmitted signal amplifying circuit, and the second end of the control unit is a received signal amplifying circuit;

the control unit specifically comprises a controller and a transmission control area; the transmission control area comprises a single-chip microcomputer (SCM), a signal generator and the transmitted signal amplifying circuit connected in sequence; and the controller is connected to the SCM;

the SCM is configured to parse an instruction issued by the controller, and send the parsed instruction to the signal generator;

the signal generator is configured to generate a corresponding sine wave signal according to the parsed instruction, and send the sine wave signal to the transmitted signal amplifying circuit;

the transmitted signal amplifying circuit is configured to amplify the sine wave signal, and send the amplified sine wave signal to the transmitting end acoustic wave probe, and the transmitting end acoustic wave probe transmits the sine wave signal as an acoustic wave signal to the core and the receiving end acoustic wave probe;

the control unit further comprises a receiving control area; the receiving control area comprises the received signal amplifying circuit and a data acquisition circuit connected in sequence; and the data acquisition circuit is further connected to the controller and the SCM;

the received signal amplifying circuit is configured to amplify the first acoustic wave signal received by the receiving end acoustic wave probe, and send the amplified first acoustic wave signal to the data acquisition circuit;

the data acquisition circuit receives an adjustment instruction from the SCM, and is configured to acquire the second acoustic wave signal and the amplified first acoustic wave signal of different frequencies received by the receiving end acoustic wave probe;

the data acquisition circuit is further configured to:

normalize the acquired first acoustic wave signal and second acoustic wave signal into a normalized signal;

filter an alternating current (AC) signal in the normalized signal through a filter in the data acquisition circuit to acquire a direct current (DC) signal; and send the DC signal to the controller;

the normalized signal is calculated by multiplying a first signal and a second signal, wherein the first signal is obtained by normalizing the first acoustic wave signal and the second signal is obtained by normalizing the second acoustic wave signal.

2. The multi-frequency acoustic velocity measurement device for the core according to claim 1, wherein the control unit determines the acoustic velocity of the core according to the acoustic wave signals received by the receiving end acoustic wave probe by:

determining a time for the first acoustic wave signal to pass through the core; and determining the acoustic velocity based on the time and a length of the core.

3. The multi-frequency acoustic velocity measurement device for the core according to claim 2, wherein the time for the first acoustic wave signal to pass through the core is determined by:

$$S=\sin(2\pi f(t+kT));$$

wherein, S is the DC signal; f is a frequency of the first acoustic wave signal; t is the time for the first acoustic wave signal to pass through the core; k is a number of cycles of the first acoustic wave signal; and T is a cycle at a corresponding frequency.

* * * * *

UNITED STATES PATENT AND TRADEMARK OFFICE
CERTIFICATE OF CORRECTION

| | | |
|---|---|---|
| PATENT NO. | : 11,371,962 B1 | |
| APPLICATION NO. | : 17/646151 | |
| DATED | : June 28, 2022 | |
| INVENTOR(S) | : Yijian Chen et al. | |

It is certified that error appears in the above-identified patent and that said Letters Patent is hereby corrected as shown below:

On the Title Page

The name of 2nd Assignee should be:
--HAOHAN WELL COMPLETION&LOGGING SCIENCE AND TECHNOLOGY LIMITED COMPANY--

Signed and Sealed this
Twenty-second Day of November, 2022

Katherine Kelly Vidal
*Director of the United States Patent and Trademark Office*